US012752114B2

(12) United States Patent
Smith et al.

(10) Patent No.: US 12,752,114 B2
(45) Date of Patent: Oct. 6, 2026

(54) COCHLEAR IMPLANTS HAVING MRI-COMPATIBLE MAGNET APPARATUS

(71) Applicant: ADVANCED BIONICS AG, Staefa (CH)

(72) Inventors: James George Elcoate Smith, Santa Clarita, CA (US); Sung Jin Lee, Valencia, CA (US)

(73) Assignee: Advanced Bionics AG, Staefa (CH)

( * ) Notice: Subject to any disclaimer, the term of this patent is extended or adjusted under 35 U.S.C. 154(b) by 251 days.

(21) Appl. No.: 18/691,947

(22) PCT Filed: Oct. 12, 2021

(86) PCT No.: PCT/US2021/054640

§ 371 (c)(1),
(2) Date: Mar. 14, 2024

(87) PCT Pub. No.: WO2023/063934

PCT Pub. Date: Apr. 20, 2023

(65) Prior Publication Data

US 2024/0342473 A1 Oct. 17, 2024

(51) Int. Cl.

| | |
|---|---|
| ***A61N 1/36*** | (2006.01) |
| ***A61N 1/05*** | (2006.01) |
| ***A61N 1/375*** | (2006.01) |
| ***A61N 1/378*** | (2006.01) |

(52) U.S. Cl.

CPC ....... *A61N 1/36038* (2017.08); *A61N 1/0541* (2013.01); *A61N 1/375* (2013.01); *A61N 1/3758* (2013.01); *A61N 1/378* (2013.01)

(58) Field of Classification Search

None

See application file for complete search history.

(56) References Cited

U.S. PATENT DOCUMENTS

| | | | |
|---|---|---|---|
| 4,214,366 | A | 7/1980 | Laban |
| 4,352,960 | A | 10/1982 | Dormer et al. |
| 4,595,390 | A | 6/1986 | Hakim et al. |
| 4,606,329 | A | 8/1986 | Hough |

(Continued)

FOREIGN PATENT DOCUMENTS

| | | | |
|---|---|---|---|
| CN | 212542072 | U | 2/2021 |
| DE | 202006017662 | U1 | 9/2007 |

(Continued)

OTHER PUBLICATIONS

PCT International Search and Written Opinion dated Jun. 24, 2022 for PCT App. Ser. No. PCT/US2021/054640.

(Continued)

*Primary Examiner* — Michael W Kahelin

(74) *Attorney, Agent, or Firm* — Henricks Slavin LLP

(57) ABSTRACT

A magnet apparatus including a case defining a central axis, a frame, defining a receptacle, within the case and rotatable about the central axis of the case, a magnet holder within the receptacle and including a plurality of tubes that together define an integral structure, and a plurality of elongate diametrically magnetized magnets that are respectively located in the plurality of tubes, the magnets defining a longitudinal axis and a N-S direction and being rotatable about the longitudinal axis relative to the tubes.

21 Claims, 10 Drawing Sheets

(56) References Cited

U.S. PATENT DOCUMENTS

| | | | |
|---|---|---|---|
| 4,612,915 | A | 9/1986 | Hough et al. |
| 4,618,949 | A | 10/1986 | Lister |
| RE32,947 | E | 6/1989 | Dormer et al. |
| 5,290,281 | A | 3/1994 | Tschakaloff |
| 5,755,762 | A | 5/1998 | Bush |
| 5,824,022 | A | 10/1998 | Zilberman et al. |
| 5,945,762 | A | 8/1999 | Chen et al. |
| 6,032,677 | A | 3/2000 | Blechman et al. |
| 6,178,353 | B1 | 1/2001 | Griffith et al. |
| 6,190,305 | B1 | 2/2001 | Ball et al. |
| 6,217,508 | B1 | 4/2001 | Ball et al. |
| 6,227,820 | B1 | 5/2001 | Jarvik |
| 6,292,678 | B1 | 9/2001 | Hall et al. |
| 6,348,070 | B1 | 2/2002 | Teissl et al. |
| 6,358,281 | B1 | 3/2002 | Berrang et al. |
| 6,461,288 | B1 | 10/2002 | Holcomb |
| 6,599,321 | B2 | 7/2003 | Hyde, Jr. |
| 6,838,963 | B2 | 1/2005 | Zimmerling |
| 7,091,806 | B2 | 8/2006 | Zimmerling et al. |
| 7,190,247 | B2 | 3/2007 | Zimmerling |
| 7,266,208 | B2 | 9/2007 | Charvin et al. |
| 7,566,296 | B2 | 7/2009 | Zimmerling et al. |
| 7,609,061 | B2 | 10/2009 | Hochmair |
| 7,642,887 | B2 | 1/2010 | Zimmerling |
| 7,680,525 | B1 | 3/2010 | Damadian |
| 7,729,774 | B1 | 6/2010 | Lynch et al. |
| 7,774,069 | B2 | 8/2010 | Olson et al. |
| 7,856,986 | B2 | 12/2010 | Darley |
| 7,881,800 | B2 | 2/2011 | Daly et al. |
| 7,976,453 | B2 | 7/2011 | Zimmerling et al. |
| 8,013,699 | B2 | 9/2011 | Zimmerling |
| 8,027,735 | B1 | 9/2011 | Tziviskos et al. |
| 8,118,725 | B2 | 2/2012 | Zimmerling et al. |
| 8,255,058 | B2 | 8/2012 | Gibson et al. |
| 8,340,774 | B2 | 12/2012 | Hochmair et al. |
| 8,634,909 | B2 | 1/2014 | Zimmerling et al. |
| 8,733,494 | B1 | 5/2014 | Leigh |
| 8,734,475 | B2 | 5/2014 | Ekvall et al. |
| 8,744,106 | B2 | 6/2014 | Ball |
| 8,758,394 | B2 | 6/2014 | Zimmerling et al. |
| 8,787,608 | B2 | 7/2014 | Van Himbeeck et al. |
| 8,790,409 | B2 | 7/2014 | Van den Heuvel et al. |
| 8,825,171 | B1 | 9/2014 | Thenuwara et al. |
| 8,891,795 | B2 | 11/2014 | Andersson |
| 8,897,475 | B2 | 11/2014 | Ball et al. |
| RE45,701 | E | 9/2015 | Zimmerling et al. |
| 9,126,010 | B2 | 9/2015 | Shah et al. |
| 9,162,054 | B2 | 10/2015 | Dalton |
| 9,227,064 | B2 | 1/2016 | Duftner |
| 9,295,425 | B2 | 3/2016 | Ball |
| 9,314,625 | B2 | 4/2016 | Kasic, II et al. |
| 9,352,149 | B2 | 5/2016 | Thenuwara et al. |
| RE46,057 | E | 7/2016 | Zimmerling et al. |
| 9,392,382 | B1 | 7/2016 | Nagl et al. |
| 9,420,388 | B2 | 8/2016 | Ball |
| 9,549,267 | B2 | 1/2017 | Nagl et al. |
| 9,615,181 | B2 | 4/2017 | Nagl et al. |
| 9,656,065 | B2 | 5/2017 | Tourrel et al. |
| 9,919,154 | B2 | 3/2018 | Lee |
| 9,931,501 | B2 | 4/2018 | Smyth |
| 10,300,276 | B2 | 5/2019 | Lee et al. |
| 10,463,849 | B2 | 11/2019 | Lee et al. |
| 10,532,209 | B2 | 1/2020 | Lee et al. |
| 10,646,712 | B2 | 5/2020 | Smith et al. |
| 10,646,718 | B2 | 5/2020 | Smith et al. |
| 10,806,936 | B2 | 10/2020 | Crawford et al. |
| 10,821,279 | B2 | 11/2020 | Lee et al. |
| 11,097,095 | B2 | 8/2021 | Smith et al. |
| 11,287,495 | B2 | 3/2022 | Smith et al. |
| 11,304,015 | B2 | 4/2022 | Haagerup |
| 11,364,384 | B2 | 6/2022 | Smith et al. |
| 11,471,679 | B2 | 10/2022 | Smith et al. |
| 11,476,025 | B2 | 10/2022 | Lee et al. |
| 11,638,823 | B2 | 5/2023 | Brehm et al. |
| 11,752,338 | B2 | 9/2023 | Smith et al. |
| 11,779,754 | B2 | 10/2023 | Smith et al. |
| 11,986,656 | B2 | 5/2024 | Lee et al. |
| 12,350,493 | B2 | 7/2025 | Smith et al. |
| 12,364,857 | B2 | 7/2025 | Crawford et al. |
| 12,440,668 | B2 | 10/2025 | Lee et al. |
| 12,544,579 | B2 | 2/2026 | Smith et al. |
| 2004/0012470 | A1 | 1/2004 | Zimmerling et al. |
| 2004/0059423 | A1 | 3/2004 | Barnes et al. |
| 2004/0063072 | A1 | 4/2004 | Honkura et al. |
| 2004/0210103 | A1 | 10/2004 | Westerkull |
| 2004/0260362 | A1 | 12/2004 | Darley |
| 2005/0001703 | A1 | 1/2005 | Zimmerling |
| 2005/0004629 | A1 | 1/2005 | Gibson et al. |
| 2005/0062567 | A1 | 3/2005 | Zimmerling et al. |
| 2006/0015155 | A1 | 1/2006 | Charvin et al. |
| 2006/0116743 | A1 | 6/2006 | Gibson et al. |
| 2006/0244560 | A1 | 11/2006 | Zimmerling et al. |
| 2007/0053536 | A1 | 3/2007 | Westerkull |
| 2007/0126540 | A1 | 6/2007 | Zimmerling |
| 2008/0097496 | A1 | 4/2008 | Chang et al. |
| 2008/0103350 | A1 | 5/2008 | Farone |
| 2008/0192968 | A1 | 8/2008 | Ho et al. |
| 2008/0195178 | A1 | 8/2008 | Kuzma |
| 2009/0048580 | A1 | 2/2009 | Gibson |
| 2009/0099403 | A1 | 4/2009 | Zimmerling et al. |
| 2009/0134721 | A1 | 5/2009 | Zimmerling |
| 2009/0248155 | A1 | 10/2009 | Parker |
| 2009/0287278 | A1 | 11/2009 | Charvin |
| 2010/0004716 | A1 | 1/2010 | Zimmerling et al. |
| 2010/0036458 | A1 | 2/2010 | Dufter et al. |
| 2010/0046778 | A1 | 2/2010 | Crawford et al. |
| 2010/0046779 | A1 | 2/2010 | Crawford et al. |
| 2011/0009925 | A1 | 1/2011 | Leigh et al. |
| 2011/0022120 | A1 | 1/2011 | Ball et al. |
| 2011/0068885 | A1 | 3/2011 | Fullerton et al. |
| 2011/0218605 | A1 | 9/2011 | Cryer |
| 2011/0224756 | A1 | 9/2011 | Zimmerling et al. |
| 2011/0255731 | A1 | 10/2011 | Ball |
| 2011/0264172 | A1 | 10/2011 | Zimmerling et al. |
| 2012/0296155 | A1 | 11/2012 | Ball |
| 2013/0079749 | A1 | 3/2013 | Overstreet et al. |
| 2013/0150657 | A1 | 6/2013 | Leigh et al. |
| 2013/0184804 | A1 | 7/2013 | Dalton |
| 2013/0281764 | A1 | 10/2013 | Bjorn et al. |
| 2013/0343588 | A1 | 12/2013 | Karunasiri |
| 2014/0005750 | A1 | 1/2014 | Garnham et al. |
| 2014/0012069 | A1 | 1/2014 | Ball |
| 2014/0012070 | A1 | 1/2014 | Nagl et al. |
| 2014/0012071 | A1 | 1/2014 | Nagl et al. |
| 2014/0012349 | A1 | 1/2014 | Zimmerling |
| 2014/0121449 | A1 | 5/2014 | Kasic et al. |
| 2014/0121586 | A1 | 5/2014 | Bertrand et al. |
| 2014/0163692 | A1 | 6/2014 | Van den Heuvel et al. |
| 2014/0336447 | A1 | 11/2014 | Bjorn et al. |
| 2014/0343626 | A1 | 11/2014 | Thenuwara et al. |
| 2015/0025613 | A1 | 1/2015 | Nyberg et al. |
| 2015/0073205 | A1 | 3/2015 | Ball et al. |
| 2015/0087892 | A1 | 3/2015 | Tourrel et al. |
| 2015/0094521 | A1 | 4/2015 | Neuman et al. |
| 2015/0100109 | A1 | 4/2015 | Feldman et al. |
| 2015/0112407 | A1 | 4/2015 | Hartley et al. |
| 2015/0265842 | A1 | 9/2015 | Ridler |
| 2015/0320523 | A1 | 11/2015 | Way et al. |
| 2015/0367126 | A1 | 12/2015 | Smyth |
| 2015/0374989 | A1 | 12/2015 | Hazard et al. |
| 2015/0382114 | A1 | 12/2015 | Andersson et al. |
| 2016/0008596 | A1 | 1/2016 | Gibson et al. |
| 2016/0023006 | A1 | 1/2016 | Ridler et al. |
| 2016/0037273 | A1 | 2/2016 | Gustafsson |
| 2016/0144170 | A1 | 5/2016 | Gibson et al. |
| 2016/0205484 | A1 | 7/2016 | Nagl et al. |
| 2016/0213936 | A1 | 7/2016 | Heerlein et al. |
| 2016/0310737 | A1 | 10/2016 | Tourrel et al. |
| 2016/0361537 | A1 | 12/2016 | Leigh et al. |
| 2016/0381473 | A1 | 12/2016 | Gustafsson |
| 2016/0381474 | A1 | 12/2016 | Gustafsson et al. |
| 2017/0050027 | A1 | 2/2017 | Andersson et al. |
| 2017/0078808 | A1 | 3/2017 | Kennes |
| 2017/0156010 | A1 | 6/2017 | Verma et al. |

(56) References Cited

U.S. PATENT DOCUMENTS

| | | | |
|---|---|---|---|
| 2017/0173334 | A1 | 6/2017 | Zimmerling |
| 2017/0239476 | A1 | 8/2017 | Lee |
| 2017/0251312 | A1 | 8/2017 | Crawford et al. |
| 2017/0347208 | A1 | 11/2017 | Jurkiewicz |
| 2018/0028818 | A1 | 2/2018 | Anderson et al. |
| 2018/0056084 | A1 | 3/2018 | Alam |
| 2018/0110985 | A1 | 4/2018 | Walter |
| 2018/0110986 | A1 | 4/2018 | Lee |
| 2018/0133486 | A1 | 5/2018 | Smith |
| 2018/0146308 | A1 | 5/2018 | Leigh et al. |
| 2018/0160241 | A1 | 6/2018 | Gustafsson et al. |
| 2018/0160242 | A1 | 6/2018 | Sriskandarajah |
| 2018/0185634 | A1 | 7/2018 | Smyth |
| 2018/0249262 | A1 | 8/2018 | Santek |
| 2018/0270591 | A1 | 9/2018 | Kennes |
| 2018/0296826 | A1 | 10/2018 | Lee et al. |
| 2018/0303602 | A1 | 10/2018 | Leigh |
| 2018/0304078 | A1 | 10/2018 | Crawford et al. |
| 2018/0369586 | A1* | 12/2018 | Lee .................... A61N 1/36038 |
| 2019/0015662 | A1 | 1/2019 | Raje et al. |
| 2019/0046797 | A1* | 2/2019 | Calixto ................ A61N 1/0541 |
| 2019/0053908 | A1 | 2/2019 | Cook et al. |
| 2019/0076649 | A1 | 3/2019 | Lee et al. |
| 2019/0255316 | A1* | 8/2019 | Lee ........................... H01F 7/02 |
| 2019/0298417 | A1 | 10/2019 | Barrett et al. |
| 2020/0114151 | A1 | 4/2020 | Smith et al. |
| 2020/0230422 | A1 | 7/2020 | Gibson et al. |
| 2020/0238088 | A1 | 7/2020 | Smith et al. |
| 2020/0330777 | A1 | 10/2020 | Smith et al. |
| 2020/0391023 | A1 | 12/2020 | Lee et al. |
| 2021/0046311 | A1 | 2/2021 | Brehm et al. |
| 2021/0106815 | A1 | 4/2021 | Smith et al. |
| 2021/0156934 | A1 | 5/2021 | Smith et al. |
| 2021/0299456 | A1 | 9/2021 | Smith et al. |
| 2021/0316136 | A1 | 10/2021 | Smith et al. |
| 2021/0339021 | A1 | 11/2021 | Brehm et al. |
| 2022/0273948 | A1 | 9/2022 | Calixto et al. |
| 2022/0280793 | A1 | 9/2022 | Smith et al. |
| 2023/0032218 | A1 | 2/2023 | Smith et al. |
| 2023/0061335 | A1 | 3/2023 | Lee et al. |
| 2023/0115968 | A1 | 4/2023 | Lee et al. |
| 2026/0054068 | A1 | 2/2026 | Smith et al. |
| 2026/0077195 | A1 | 3/2026 | Alanis et al. |

FOREIGN PATENT DOCUMENTS

| | | | |
|---|---|---|---|
| EP | 0241307 | A2 | 10/1987 |
| EP | 2117489 | B1 | 5/2010 |
| EP | 2853287 | A1 | 4/2015 |
| EP | 2560730 | B1 | 11/2016 |
| EP | 3138605 | A1 | 3/2017 |
| EP | 2098198 | B1 | 9/2017 |
| EP | 3964259 | A1 | 3/2022 |
| RU | 2727227 | C1 | 7/2020 |
| WO | WO9858990 | A1 | 12/1998 |
| WO | WO03081976 | A2 | 10/2003 |
| WO | WO03092326 | A1 | 11/2003 |
| WO | WO2004004416 | A1 | 1/2004 |
| WO | WO2004014269 | A1 | 2/2004 |
| WO | WO2004014270 | A1 | 2/2004 |
| WO | WO2007024657 | A2 | 3/2007 |
| WO | WO2009124045 | A1 | 10/2009 |
| WO | WO2009124174 | A2 | 10/2009 |
| WO | WO2009149069 | A2 | 12/2009 |
| WO | WO2010000027 | A1 | 1/2010 |
| WO | WO2010083554 | A1 | 7/2010 |
| WO | WO2011011409 | A1 | 1/2011 |
| WO | WO2011109486 | A2 | 9/2011 |
| WO | WO2011133747 | A1 | 10/2011 |
| WO | WO2012010195 | A1 | 1/2012 |
| WO | WO2013043176 | A1 | 3/2013 |
| WO | WO2013063355 | A1 | 5/2013 |
| WO | WO2014011441 | A1 | 1/2014 |
| WO | WO2014011582 | A2 | 1/2014 |
| WO | WO2014046662 | A1 | 3/2014 |
| WO | WO2014164023 | A1 | 10/2014 |
| WO | WO2015065442 | A1 | 5/2015 |
| WO | WO2016016821 | A1 | 2/2016 |
| WO | WO2016190886 | A1 | 12/2016 |
| WO | WO2016191429 | A1 | 12/2016 |
| WO | WO2016207856 | A1 | 12/2016 |
| WO | WO2017027045 | A1 | 2/2017 |
| WO | WO2017027046 | A1 | 2/2017 |
| WO | WO2017029615 | A1 | 2/2017 |
| WO | WO2017034530 | A1 | 3/2017 |
| WO | WO2017046650 | A1 | 3/2017 |
| WO | WO2017087004 | A1 | 5/2017 |
| WO | WO2017105510 | A1 | 6/2017 |
| WO | WO2017105511 | A1 | 6/2017 |
| WO | WO2017105604 | A1 | 6/2017 |
| WO | WO2017172566 | A1 | 10/2017 |
| WO | WO2018190813 | A1 | 10/2018 |
| WO | WO2018191314 | A1 | 10/2018 |
| WO | WO2018199936 | A1 | 11/2018 |
| WO | WO2018200347 | A1 | 11/2018 |
| WO | WO2018217187 | A1 | 11/2018 |
| WO | WO2019027745 | A1 | 2/2019 |
| WO | WO2019083540 | A1 | 5/2019 |
| WO | WO2019160555 | A1 | 8/2019 |
| WO | WO2020092185 | A1 | 5/2020 |
| WO | WO2021201845 | A1 | 10/2021 |
| WO | WO2023063983 | A1 | 4/2023 |
| WO | WO2023064308 | A1 | 4/2023 |
| WO | WO2023113790 | A1 | 6/2023 |
| WO | WO2024043896 | A1 | 2/2024 |
| WO | WO2024080978 | A1 | 4/2024 |

OTHER PUBLICATIONS

Ju Hyun Jeon et al., "Reversing the Polarity of a Cochlear Implant Magnet After Magnetic Resonance Imaging," Auris Nasus Larynx, vol. 39, No. 4, pp. 415-417, Aug. 1, 2012.

Teissl et al., "Magentic Resonance Imaging and Cochlear Implants: Compatibility and Safety Aspects," Journal of Magnetic Resonance Imaging, Society for Magnetic Resonance Imaging, vol. 9, No. 1, pp. 26-38, Jan. 1, 1999.

* cited by examiner

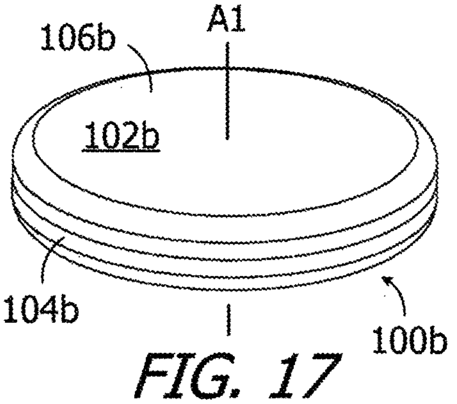
FIG. 17
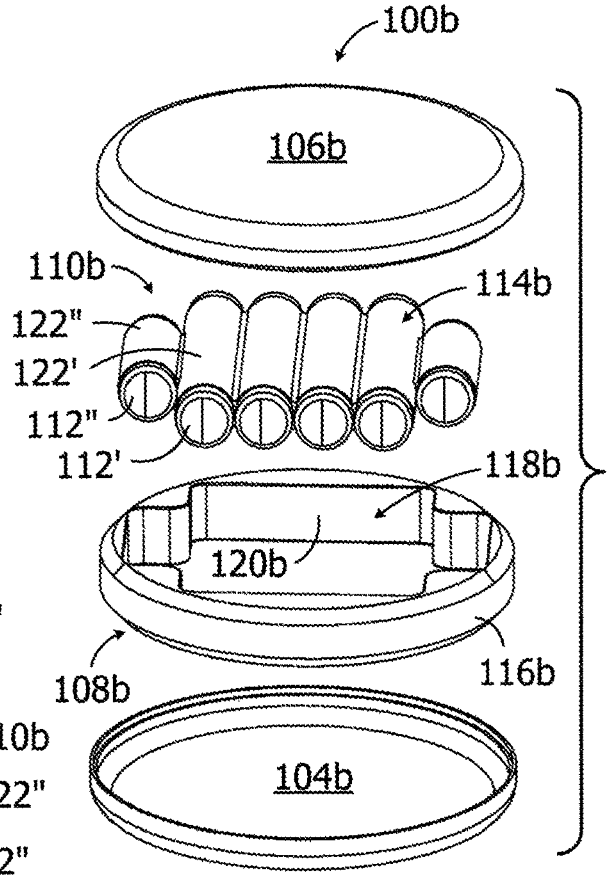
FIG. 19
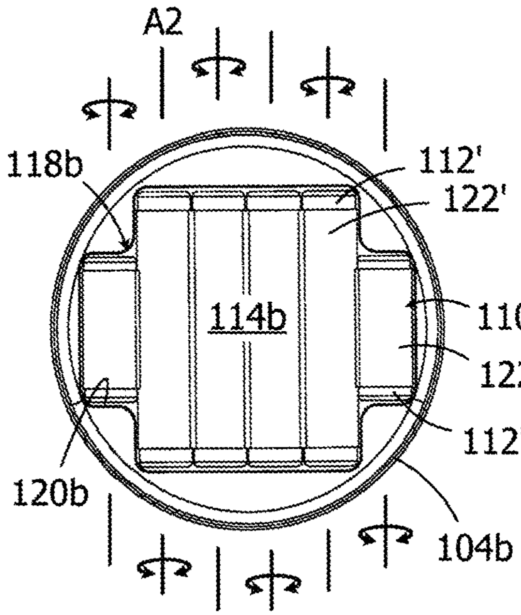
FIG. 18
FIG. 20
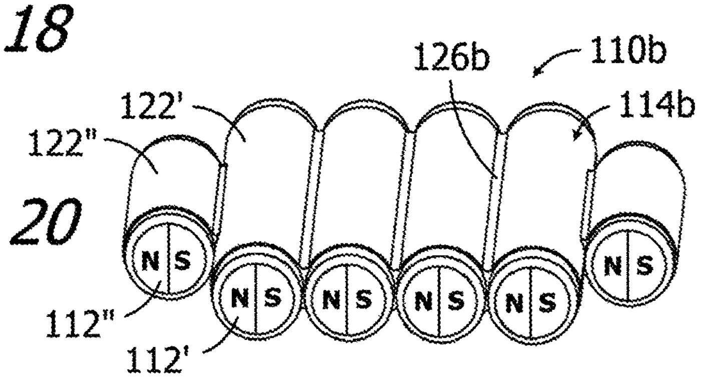
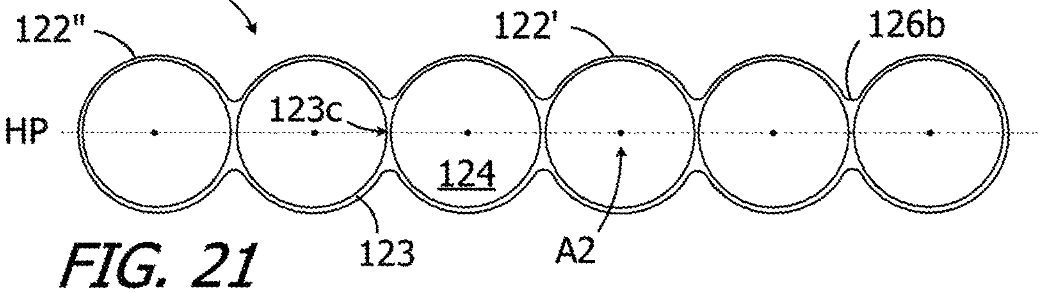
FIG. 21

COCHLEAR IMPLANTS HAVING MRI-COMPATIBLE MAGNET APPARATUS

CROSS-REFERENCE TO RELATED APPLICATIONS

This application is the U.S. National Stage of PCT App. Ser. No. PCT/US2021/054640, filed Oct. 12, 2021.

BACKGROUND

1. Field

The present disclosure relates generally to the implantable portion of implantable cochlear stimulation (or "ICS") systems.

2. Description of the Related Art

ICS systems are used to help the profoundly deaf perceive a sensation of sound by directly exciting the intact auditory nerve with controlled impulses of electrical current. Ambient sound pressure waves are picked up by an externally worn microphone and converted to electrical signals. The electrical signals, in turn, are processed by a sound processor, converted to a pulse sequence having varying pulse widths, rates and/or amplitudes, and transmitted to an implanted receiver circuit of the ICS system. The implanted receiver circuit is connected to an implantable electrode array that has been inserted into the cochlea of the inner ear, and electrical stimulation current is applied to varying electrode combinations to create a perception of sound. The electrode array may, alternatively, be directly inserted into the cochlear nerve without residing in the cochlea. A representative ICS system is disclosed in U.S. Pat. No. 5,824,022, which is entitled "Cochlear Stimulation System Employing Behind-The-Ear Sound processor With Remote Control" and incorporated herein by reference in its entirety. Examples of commercially available ICS sound processors include, but are not limited to, the Harmony™ BTE sound processor, the Naida™ CI Q Series sound processor and the Neptune™ body worn sound processor, which are available from Advanced Bionics.

As alluded to above, some ICS systems include an implantable cochlear stimulator (or "cochlear implant"), a sound processor unit (e.g., a body worn processor or behind-the-ear processor), and a microphone that is part of, or is in communication with, the sound processor unit. The cochlear implant communicates with the sound processor unit and, some ICS systems include a headpiece that is in communication with both the sound processor unit and the cochlear implant. The headpiece communicates with the cochlear implant by way of a transmitter (e.g., an antenna) on the headpiece and a receiver (e.g., an antenna) on the implant. Optimum communication is achieved when the transmitter and the receiver are aligned with one another. To that end, the headpiece and the cochlear implant may include respective positioning magnets that are attracted to one another, and that maintain the position of the headpiece transmitter over the implant receiver. The implant magnet may, for example, be located within a pocket in the cochlear implant housing. The skin and subcutaneous tissue that separates the headpiece magnet and implant magnet is sometimes referred to as the "skin flap," which is frequently 3 mm to 11 mm thick.

The present inventors have determined that conventional cochlear implants are susceptible to improvement. For example, the magnets in some conventional cochlear implants are disk-shaped and have north and south magnetic dipoles that are aligned in the axial direction of the disk. Such magnets are not compatible with magnetic resonance imaging ("MRI") systems, and may have to be surgically removed from the cochlear the implant prior to the MRI procedure and then surgically replaced thereafter. Other cochlear implants include with a diametrically magnetized disk-shaped magnet that is rotatable relative to the remainder of the implant about its central axis, and that has a N-S orientation which is perpendicular to the central axis. The present inventors have determined that diametrically magnetized disk-shaped magnets are less than optimal because a dominant magnetic field, such as the MRI magnetic field, that is misaligned by at least 30° or more from the N-S direction of the magnet may demagnetize the magnet or generate an amount of torque on the magnet that is sufficient to dislodge or reverse the magnet and/or dislocate the associated cochlear implant and/or cause excessive discomfort to the patient.

More recently, cochlear implants with MRI-compatible magnet apparatus have been introduced. The MRI-compatible magnet apparatus have a case defining a central axis, a frame within the case that is rotatable relative to the case about the central axis, and a plurality of elongate diametrically magnetized magnets that are located in the frame and rotatable about their respective longitudinal axis relative to the frame. Examples of MRI-compatible magnet apparatus may be found in U.S. Pat. Nos. 9,919,154, 10,463,849, and 10,532,209.

Although such MRI-compatible magnet apparatus have proven to be a significant advance in the art, the present inventors have determined that they are susceptible to improvement. For example, the elongate diametrically magnetized magnets may be located within low friction tubes formed from a low friction material such as polyetheretherketone (PEEK) to facilitate rotation of the magnets relative to one another. The magnet/tube subassemblies must then the properly positioned relative to one another so that they can be combined with the frame. The present inventors have determined, however, that aligning the individual magnet/tube subassemblies with one another can be difficult. The relatively high strength of the magnets sometimes results in the magnets slamming against one another during assembly, which can damage the magnets. The magnets and tubes are also relatively small, and the inner diameter of the tubes may be slightly larger than the outer diameter of the magnets to facilitate insertion of the magnets into the tubes. The magnets can, due to the larger diameter, compress the portions of the tubes that are between adjacent magnets. The compression can cause the tubes, and in particular those that are between two magnets, to distend from a circular cross-section to an oval cross-section that can impede magnet rotation. There is frequently also a relatively tight fit between the between the magnets and the frame, which can also make assembly difficult.

SUMMARY

A magnet assembly in accordance with one of the present inventions may include a case defining a central axis, a frame, defining a receptacle, within the case and rotatable about the central axis of the case, a magnet holder within the receptacle and including a plurality of tubes that together define an integral structure, and a plurality of elongate diametrically magnetized magnets that are respectively located in the plurality of tubes, the magnets defining a longitudinal axis and a N-S direction and being rotatable about the longitudinal axis relative to the tubes. A cochlear implant in accordance with one of the present inventions may include a cochlear lead, an antenna, a stimulation processor, and such a magnet assembly.

A magnet assembly in accordance with one of the present inventions may include a case defining a central axis, a frame, including first and second separate frame members that together define a magnet receptacle, within the case and rotatable about the central axis of the case, and a plurality of elongate diametrically magnetized magnets that are located in the magnet receptacle, the magnets each defining a longitudinal axis and a N-S direction and being rotatable about the longitudinal axis relative to the frame. A cochlear implant in accordance with one of the present inventions may include a cochlear lead, an antenna, a stimulation processor, and such a magnet assembly.

There are a number of advantages associated with such magnet assemblies. For example, placing the magnets into a magnet holder, as opposed to placing each magnet into an individual tube, prior to placing the magnets into the case reduces the difficulty of the assembly process and also reduces the likelihood that the magnets will be damaged. The use of a frame with separate frame members allows the relatively tight fit between the between the magnets and the frame to be achieved after the magnets are in place, and also allows the frame to be used to properly align the ends of the magnets, thereby reducing assembly difficulty.

The above described and many other features of the present inventions will become apparent as the inventions become better understood by reference to the following detailed description when considered in conjunction with the accompanying drawings.

BRIEF DESCRIPTION OF THE DRAWINGS

Detailed descriptions of the exemplary embodiments will be made with reference to the accompanying drawings.

FIG. 17 is a perspective view of an implant magnet apparatus in accordance with one embodiment of a present invention.

FIG. 18 is a top view of a portion of the implant magnet apparatus illustrated in FIG. 17.

FIG. 19 is an exploded perspective view of the implant magnet apparatus illustrated in FIG. 17.

FIG. 20 is a perspective view of a portion of the implant magnet apparatus illustrated in FIG. 17.

FIG. 21 is an end view of a portion of the implant magnet apparatus illustrated in FIG. 17.

DETAILED DESCRIPTION OF THE EXEMPLARY EMBODIMENTS

Figure 1:
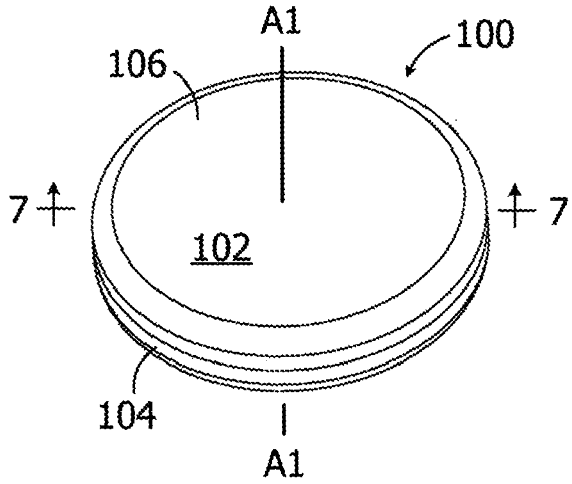
FIG. 1 is a perspective view of an implant magnet apparatus in accordance with one embodiment of a present invention.

The following is a detailed description of the best presently known modes of carrying out the inventions. This description is not to be taken in a limiting sense, but is made merely for the purpose of illustrating the general principles of the inventions.

As illustrated for example in FIGS. 1-4, an exemplary magnet apparatus 100 includes a case 102, with base 104 and a cover 106, a frame 108, and a magnet subassembly 110 within the frame. The exemplary magnet subassembly 110 includes a plurality of elongate diametrically magnetized magnets 112' and 112" (collectively "magnets 112") that define a N-S direction and are located within a holder 114. The magnets 112' are longer than the magnets 112". The magnet apparatus 100 may, in some instances, be employed a system 50 (FIG. 8) that includes a cochlear implant 200 (described below with reference to FIG. 34) with the magnet apparatus 100 and an external device such as a headpiece 400 (described below with reference to FIGS. 8 and 35).

The exemplary case 102 is disk-shaped and defines a central axis A1, which is also the central axis of the frame

108. The frame 108 is rotatable relative to the case 102 about the central axis A1 over 360°. The magnet subassembly 110 rotates with the frame 108 about the central axis A1, and does not rotate relative to the frame. Each magnet 112 is also rotatable within the holder 114 relative to the holder and the frame 108 about its own longitudinal axis A2 (also referred to as "axis A2") over 360°. The holder 114 holds all of the magnets 112 and fixes their positions relative to one another.

In the illustrated implementation, the longitudinal axes A2 are parallel to one another and are perpendicular to the central axis A1. In other implementations, the magnets within a magnet apparatus may be oriented such that the longitudinal axes thereof are at least substantially perpendicular to the central axis A1. As used herein, an axis that is "at least substantially perpendicular to the central axis" includes axes that are perpendicular to the central axis as well as axes that are slightly non-perpendicular to the central axis (i.e., axes that are offset from perpendicular by up to 5 degrees).

Figure 3:
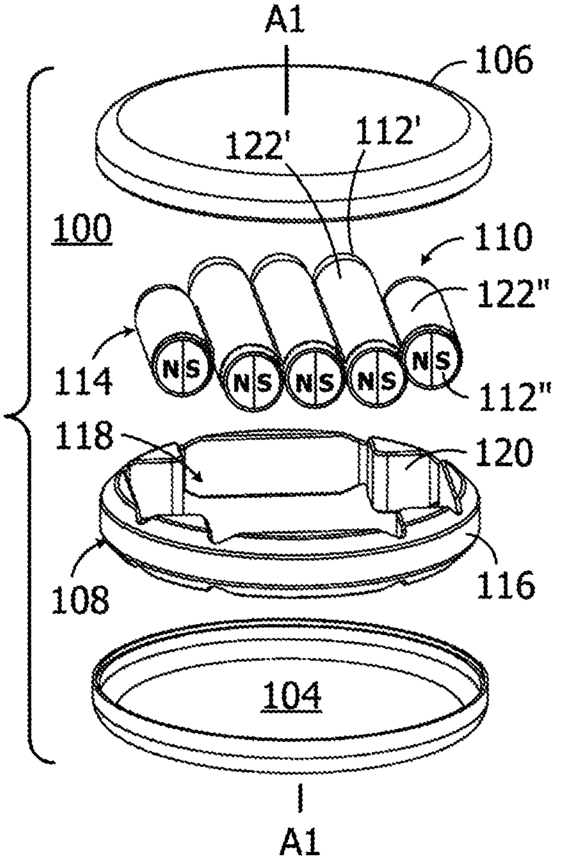
FIG. 3 is an exploded perspective view of the implant magnet apparatus illustrated in FIG. 1.
Figure 7:
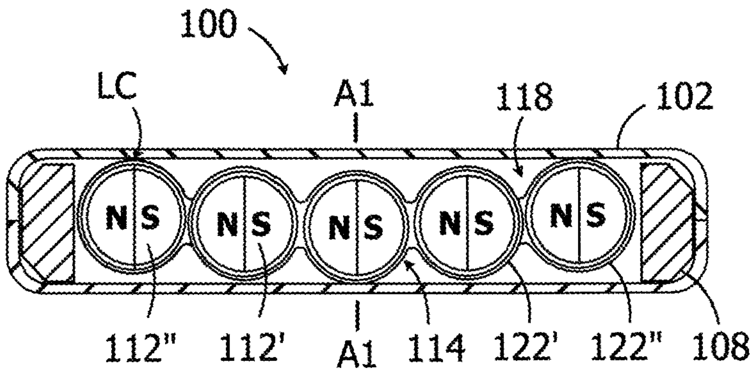
FIG. 7 is a partial section view taken along line 7-7 in FIG. 1.

Given the ability of each magnet 112 to rotate about its longitudinal axis A2, the magnets 112 align with one another in the N-S direction in the absence of an external magnetic field that is strong enough to rotate the magnets out of alignment (e.g., an MRI magnetic field or a headpiece magnetic field). The at rest N-S orientation of the magnets 112 will be perpendicular to the central axis A1, as is illustrated in FIGS. 3 and 7.

The exemplary case 102 is not limited to any particular configuration, size or shape. In the illustrated implementation, the case 102 is a two-part structure that includes the base 104 and the cover 106 which are secured to one another in such a manner that a hermetic seal is formed between the cover and the base. Suitable techniques for securing the cover 106 to the base 104 include, for example, seam welding with a laser welder. With respect to materials, the case 102 (as well as the case 102*b* described below) may be formed from biocompatible paramagnetic metals, such as titanium or titanium alloys, and/or biocompatible non-magnetic plastics such as polyether ether ketone (PEEK), low-density polyethylene (LDPE), high-density polyethylene (HDPE), ultra-high-molecular-weight polyethylene (UHMWPE), polytetrafluoroethylene (PTFE) and polyamide. In particular, exemplary metals include commercially pure titanium (e.g., Grade 2) and the titanium alloy Ti-6Al-4V (Grade 5), while exemplary metal thicknesses may range from 0.20 mm to 0.25 mm. With respect to size and shape, the case 102 (and 102*b*) may have an overall size and shape similar to that of conventional cochlear implant magnets so that the magnet apparatus 100 can be substituted for a conventional magnet in an otherwise conventional cochlear implant. The case 102 (and 102*b*) may also have an overall size and shape that is larger than that of conventional cochlear implant magnets in other embodiments. In some implementations, and depending on the number of magnets within the case 102 (or 102*b*), the diameter that may range from 9 mm to 17.40 mm and the thickness may range from 1.5 mm to 3.10 mm. The diameter of the case 102 is 15.2 mm, and the thickness is 3.10 mm, in the illustrated embodiment.

Figure 4:
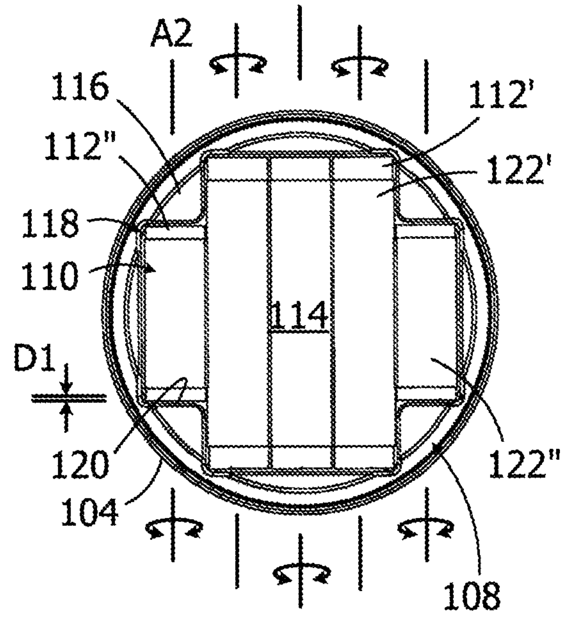
FIG. 4 is a top view of a portion of the implant magnet apparatus illustrated in FIG. 1.

The exemplary frame 108 includes a disk 116 and a magnet receptacle 118 that extends completely through the disk and is defined by inner walls 120. The magnet receptacle 118 is configured to hold the magnet subassembly 110, including all of the magnets 112 and the holder 114, and has a relatively long portion and two relatively short portions. Suitable materials for the frame 108 (as well as the frames 108*b* and 108*d* discussed below), which may be formed by machining, metal injection molding or injection molding, include paramagnetic metals, polymers and plastics such as those discussed above in the context of the case 102. Referring more specifically to FIG. 4, there may be a relatively tight fit between the between the magnet subassembly 110 and the magnet receptacle 118. For example, the distance D1 between the longitudinal ends of the magnets 112 and the inner walls 120 may be about 0.08 to 0.15 in some implementations.

Although the present inventions are not limited to any particular number, there are five elongate diametrically magnetized magnets 112 in the exemplary magnet apparatus 100 illustrated in FIGS. 1-4. Three of the otherwise identical magnets 112 are relatively long magnets 112' and two are relatively short magnets 112" in order to efficiently utilize the available volume within the case 102, as is best shown in FIG. 4. The exemplary magnets 112 are circular in a cross-section that is perpendicular to the longitudinal axis A2 and, in some instances, may have rounded corners. Suitable materials for the magnets 112 include, but are not limited to, neodymium-boron-iron and samarium-cobalt.

Figure 5:
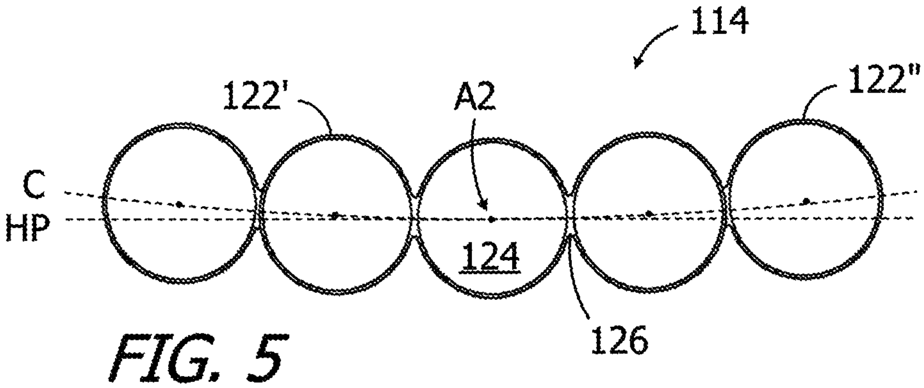
FIG. 5 is an end view of a portion of the implant magnet apparatus illustrated in FIG. 1.
Figure 6:
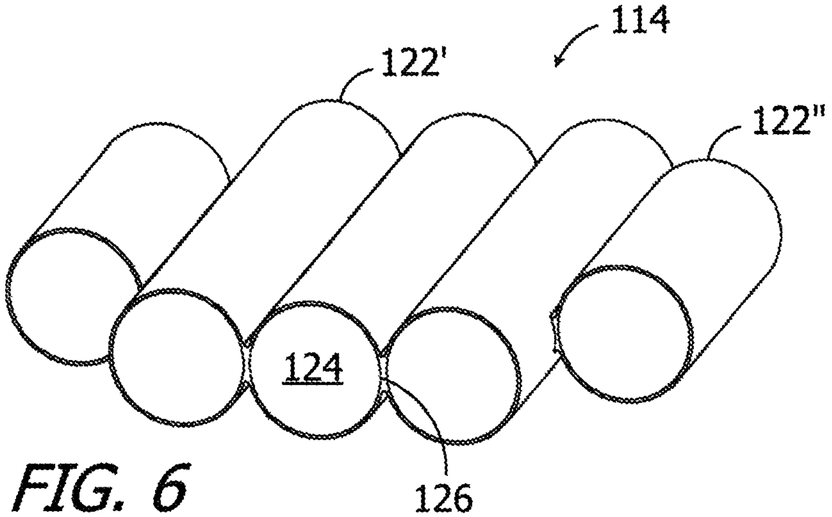
FIG. 6 is a perspective view of a portion of the implant magnet apparatus illustrated in FIG. 1.

Turning to FIGS. 5 and 6, the exemplary holder 114 includes a plurality of tubes 122, with respective lumens 124, for the plurality of magnets 112. The tubes 122 define the same longitudinal axes A2 as the magnets 112. The number of tubes 122 corresponds to the number of magnets 112 and, in the illustrated embodiment, there are three otherwise identical tubes 122' that are relatively long and two otherwise identical tubes 122" that are relatively short. The exemplary holder 114 is an integral structure wherein the tubes 122 are each attached to an adjacent tube (or tubes). As used herein, an "integral structure" is a structure where adjacent components (i.e., tubes) are attached to one another, remain attached to one another under normal use conditions, and cannot be separated from one another without destruction of the holder. Joints 126 maintain the integrity of the connection between the tubes, and prevent ovaling. In some instances, the tubes 122 may share a common wall portion, thereby reducing the overall width of the holder 114, as is discussed below with reference to FIG. 21.

Figure 2:
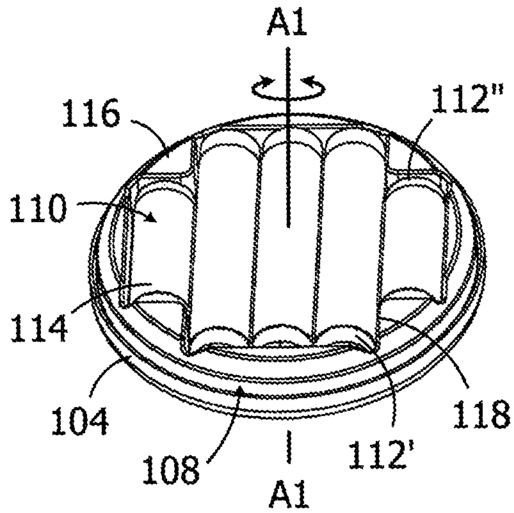
FIG. 2 is a perspective view of a portion of the implant magnet apparatus illustrated in FIG. 1.

The magnets 112 are located within the lumens 124 of the exemplary holder 114 in the manner illustrated in FIGS. 2-4 and each magnet 112 rotates about its longitudinal axis A2 relative to the associated tube 122. To facilitate such rotation, the holder 114 (as well as the magnet holders 114*a*, 114*b* and 114*c* discussed below) may be formed from low friction material including, but not limited to, polymers, such as silicone, PEEK and other plastics, PTFE, and PEEK-PTFE blends, and paramagnet metals. In the illustrated implementation, the holder 114 is a multi-lumen PEEK extrusion where all of the tubes are initially cut to the length of the relatively long tubes 122', and the relatively short tubes 122" are thereafter cut to their length. The diameter of the lumens 124 may be slightly larger (e.g., 0.03 to 0.06 larger) than the outer diameter of the magnets 112 to facilitate placement of the magnets into the holder 114 in, for example, the manner described below with reference to FIGS. 10-12.

Referring more specifically to FIG. 5, it should also be noted that exemplary holder 114 has a pre-set arcuate shape. The longitudinal axis A2 of the center tube 112 lies in a horizontal plane HP and the longitudinal axes A2 of the remaining tubes 112 are not located in the horizontal plane HP when the holder 114 is in a relaxed (i.e., unstressed) state. The axes A2 define a curve C and, as a result, fewer than all of the tubes 112 are in contact with the inner surface of the case 102 when the holder is in a relaxed state.

Referring to FIG. 7, there are only three lines of contact LC between the holder 114 due to the curvature and the inner surface of the case 102 as opposed to the minimum of five lines of contact which would be the case if the holder was not arcuate. The reduction in contact results in a corresponding reduction in friction between the holder 114 and the inner surface of the case 102, as compared to an otherwise identical magnet apparatus 100 without an arcuate holder.

Figure 7A:
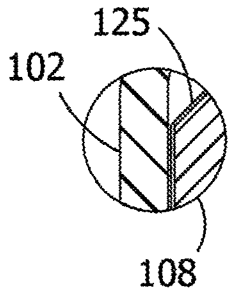
FIG. 7A is an enlarged portion of the section view illustrated in FIG. 7.

Friction may be further reduced by coating the inner surfaces of the case 102 (and other cases discussed below) and/or the surfaces of the frame 108 with a lubricious layer. The lubricious layer may be in the form of a specific finish of the surface that reduces friction, as compared to an unfinished surface, or may be a coating of a lubricious material such as diamond-like carbon (DLC), titanium nitride (TiN), PTFE, polyethylene glycol (PEG), Parylene, fluorinated ethylene propylene (FEP) and electroless nickel sold under the tradenames Nedox® and Nedox PF™. The DLC coating, for example, may be only 0.5 to 5 microns thick. In those instances where the base 104 and a cover 106 are formed by stamping, the finishing process may occur prior to stamping. Micro-balls, biocompatible oils and lubricating powders may also be added to the interior of the case to reduce friction. In the illustrated implementation, the surfaces of the frame 108 may be coated with a lubricious layer 125 (e.g., DLC), while the inner surfaces of the case 102 do not include a lubricious layer, as shown in FIGS. 7 and 7A. The lubricious layer 125 reduces friction between the case 102 and frame 108, while the low friction holder 114 reduces friction between adjacent magnets 112 as well as between the case 102 and the magnets 112.

As shown in FIG. 7, absent an external magnetic field that is strong enough to rotate the magnets 112 out of alignment (e.g., an MRI magnetic field or a headpiece magnetic field), the magnets of the exemplary magnet apparatus 100 will remain substantially aligned with one another in the N-S direction and the N-S orientation of each magnet will be perpendicular or close to perpendicular to the central axis A1 of the case 102. The magnets are also arranged an arcuate group defined by the holder 114.

Figure 8:
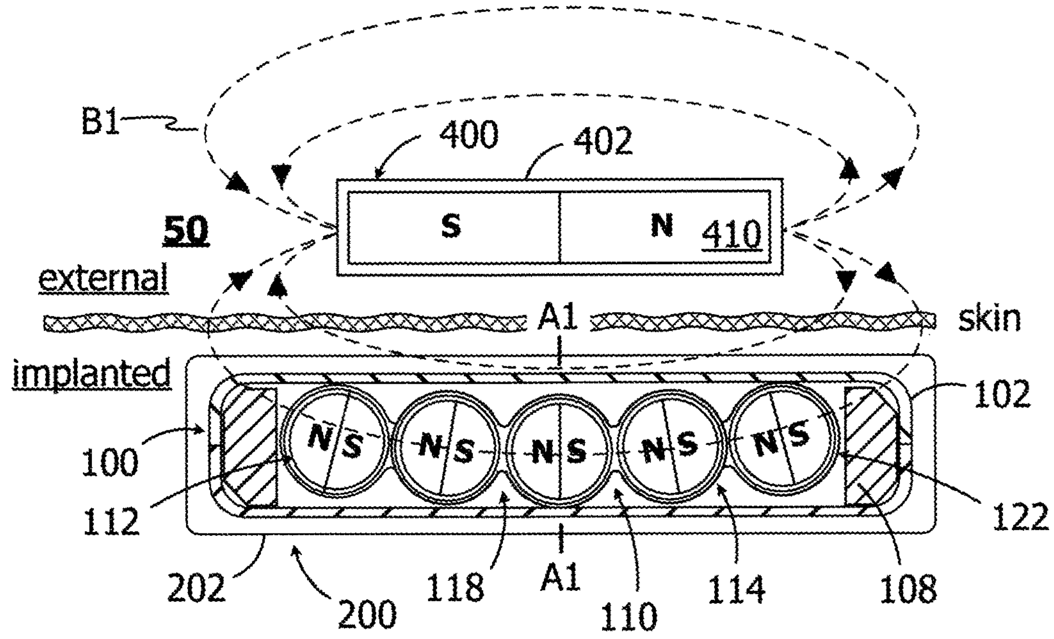
FIG. 8 is a partial section view of a system including a headpiece and an implant with the magnet apparatus illustrated in FIG. 1.

Referring to FIG. 8, the exemplary magnet apparatus 100 may part of a cochlear implant 200 with a housing 202 (described below with reference to FIG. 34) that is employed in conjunction with an external device such as a headpiece 400 (described below with reference to FIG. 35) in a system 50. The exemplary headpiece 400 includes, among other things, a housing 402 and a magnetized disk-shaped positioning magnet 410. Here, the strength of the dominant headpiece magnetic field B1 causes the magnets 112 to rotate slightly about axis A2 (FIGS. 4 and 5) from the at rest orientations illustrated in FIG. 7 to the orientations illustrated in FIG. 8. The magnet holder 114 will, as a result of its preset shape, remain unstressed. The frame 108 will also rotate about axis A1 as necessary to align the magnetic fields of the magnets 112 with the N-S direction of the magnetic field B1.

Figure 9:
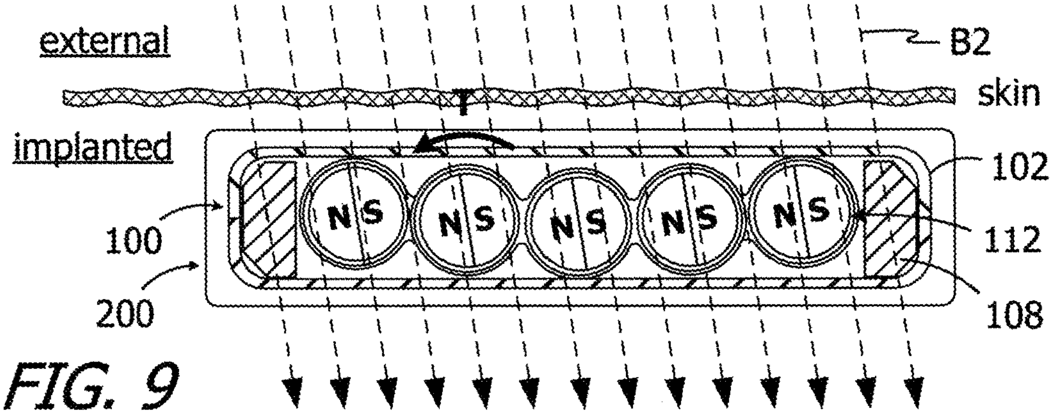
FIG. 9 is a partial section view similar to FIG. 8 with the implant in an MRI magnetic field.

Turning to FIG. 9, when exposed to a dominant MRI magnetic field B2, the torque T on the magnets 112 will rotate the magnets about their axis A2 (FIG. 4), thereby aligning the magnetic fields of the magnets 112 with the MRI magnetic field B2. The frame 108 will also rotate about axis A1 as necessary to align the magnetic fields of the magnets 112 with the MRI magnetic field B2. When the magnet apparatus 100 is removed from the MRI magnetic field B2, the magnetic attraction between the magnets 112 will cause the magnets to rotate about axis A2 back to the orientation illustrated in FIG. 7, where they are substantially aligned with one another in the N-S direction and the N-S orientation of the magnets is close to perpendicular to the central axis A1 of the case 102.

Figure 10:
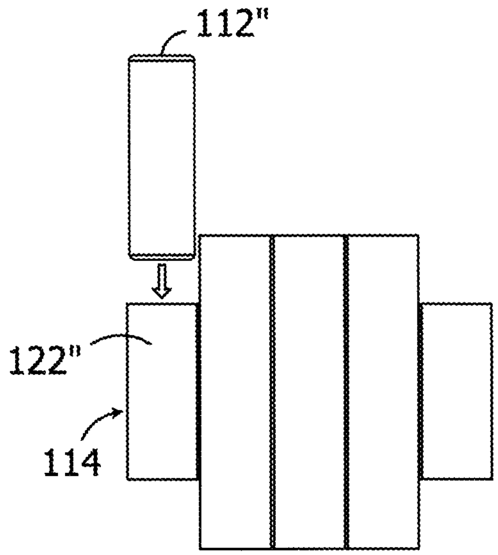
FIGS. 10-12 are top views showing an exemplary method of assembling a portion of the implant magnet apparatus illustrated in FIG. 1.
Figure 11:
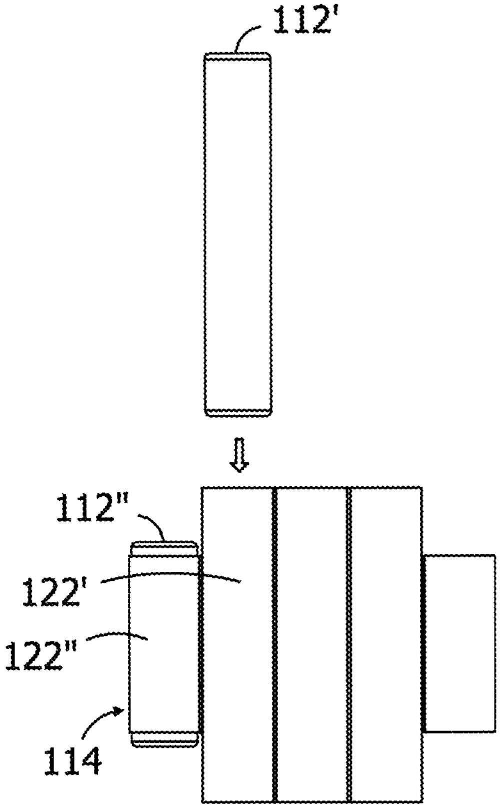
Figure 12:
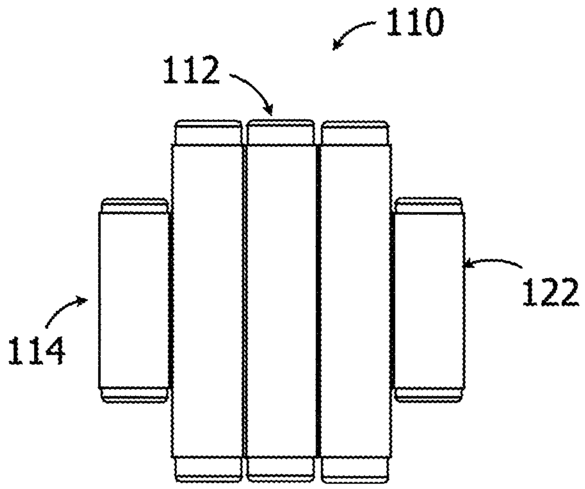
Figure 13:
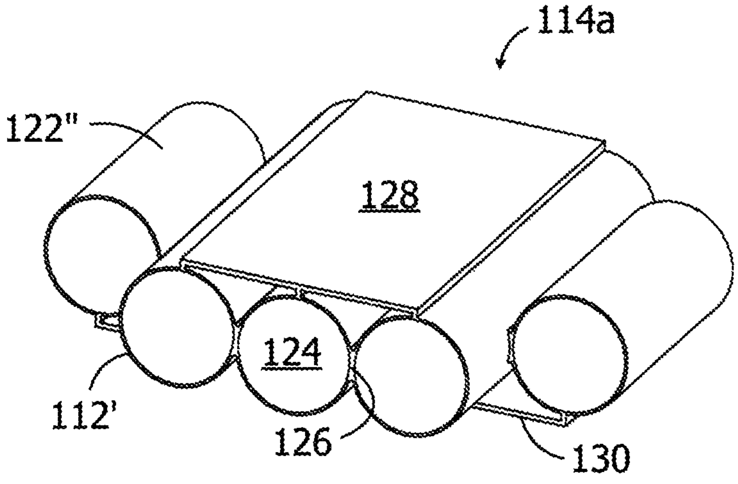
FIG. 13 is a perspective view of a portion of an implant magnet apparatus in accordance with one embodiment of a present invention.
Figure 14:
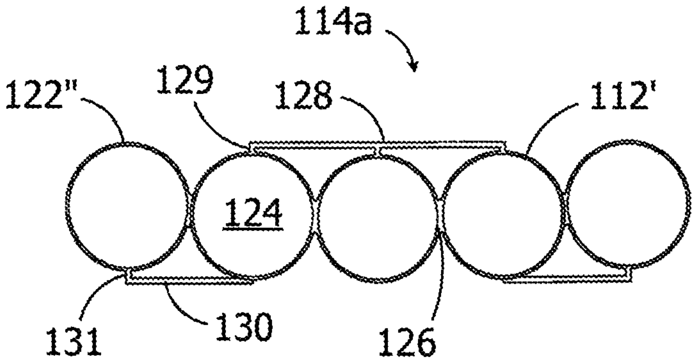
FIG. 14 is an end view of the portion of the implant magnet apparatus illustrated in FIG. 13.
Figure 15:
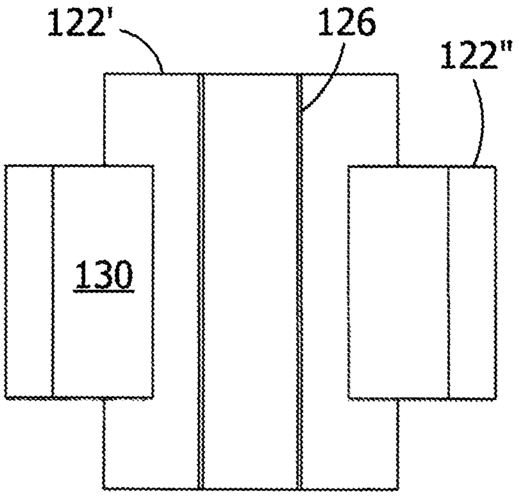
FIG. 15 is a bottom view of the portion of the implant magnet apparatus illustrated in FIG. 13.
Figure 16:
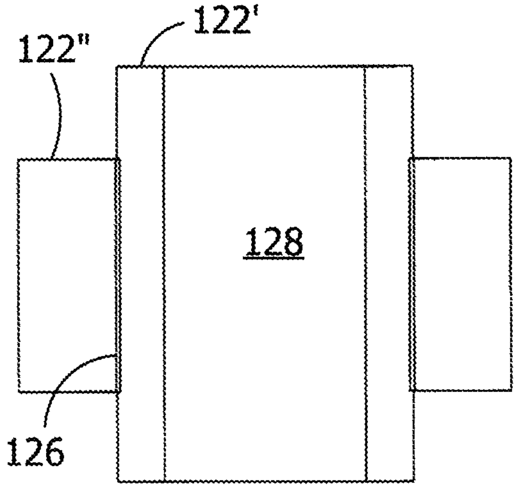
FIG. 16 is a top view of the portion of the implant magnet apparatus illustrated in FIG. 13.
Figure 22:
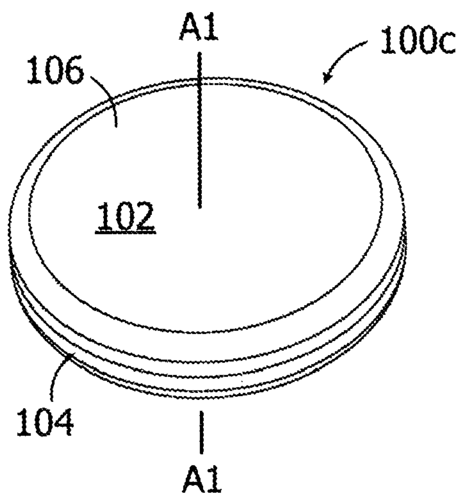
FIG. 22 is a perspective view of an implant magnet apparatus in accordance with one embodiment of a present invention.
Figure 23:
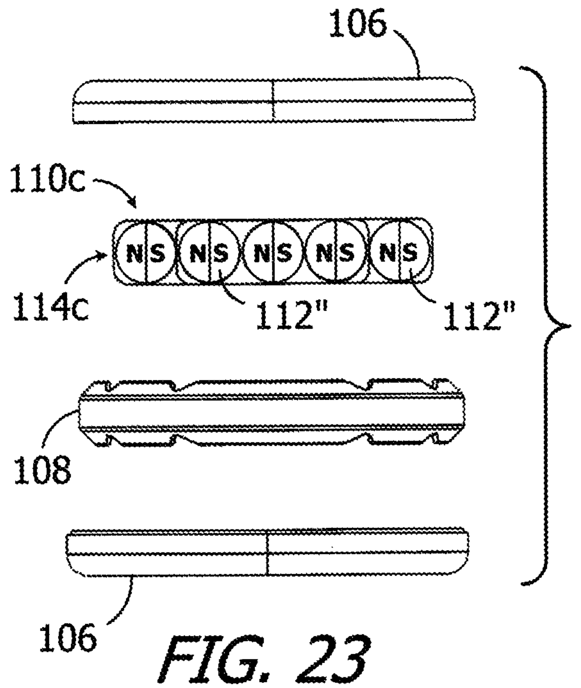
FIG. 23 is an exploded side view of the implant magnet apparatus illustrated in FIG. 22.
Figure 24:
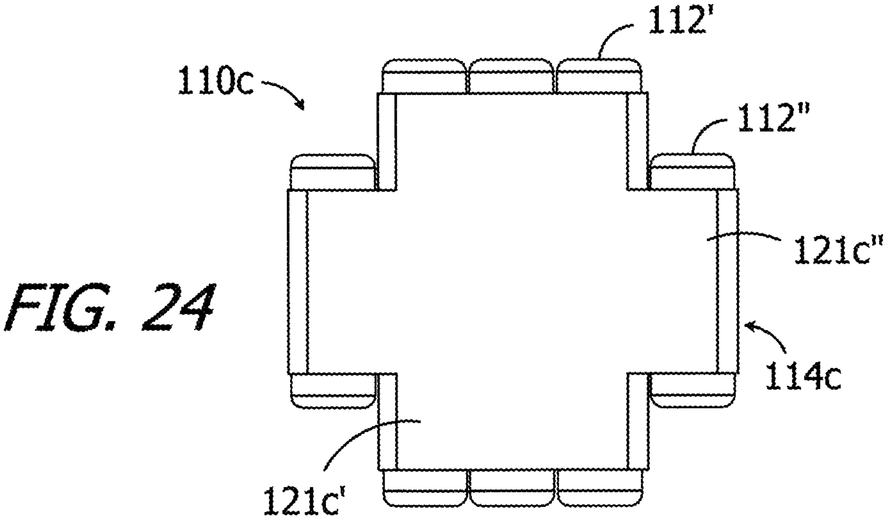
FIG. 24 is a top view of a portion of the implant magnet apparatus illustrated in FIG. 22.
Figure 25:
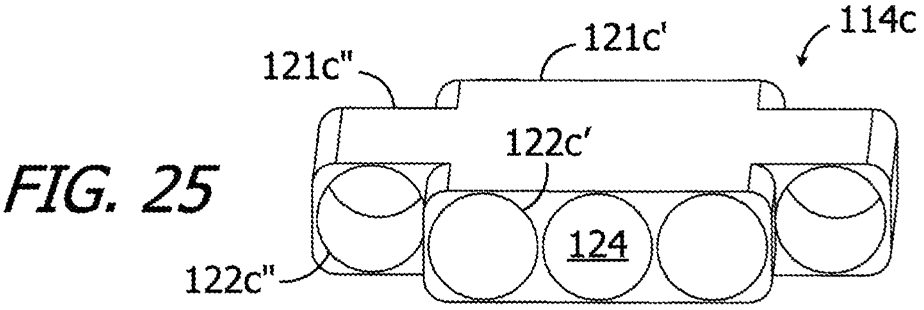
FIG. 25 is a perspective view of a portion of the implant magnet apparatus illustrated in FIG. 22.

As illustrated for example in FIGS. 10-12, the exemplary magnet subassembly 110 may be assembled by placing the relatively long magnets 112' into the relatively long tubes 122' of the holder 114 and placing the relatively short magnets 112" into the relatively short tubes 122". The technician should align the ends of longer magnets 112' with one another, align the ends of shorter magnets 112" with one another, and center the magnets relative to the holder 114 to facilitate placement into the frame 108. During assembly of the associated magnet apparatus, e.g., magnet apparatus 100, the frame 108 may be placed into the case base 104 and the completed magnet subassembly 110 may be placed into frame. Alternatively, the magnet subassembly 110 may be placed into the frame 108, and then both may be simultaneously placed into the case base 104. Either way, the assembly process is far easier than a process that involves placing separate magnets one at a time into the frame.

Another exemplary magnet holder is generally represented by reference numeral 114*a* in FIGS. 13-16. The exemplary magnet holder 114*a* is substantially similar to magnet holder 114 and similar elements are represented by similar reference numerals. Here, however, the magnet holder 114*a* also includes reinforcement panels 128 and 130 that help maintain the arcuate shape defined by the tubes 112. The exemplary reinforcement panel 128 is the same length as the relatively long tubes 112', and is secured to the relatively long tubes 112' by rails 129. The exemplary reinforcement panels 130 are the same length as the relatively short tubes 112", are secured to the relatively short tubes 112" by rails 131, and are secured directly to the relatively long tubes 112'. The magnet holder 114*a* may be formed from the same materials as the magnet holder 114. Suitable materials for the holder 114*a* include those described above with reference to holder 114. In the illustrated implementation, the holder 114*a* is a multi-lumen PEEK extrusion where all of the tubes and reinforcement panels are initially cut to the length of the relatively long tubes 122' and reinforcement panel 128, and the relatively short tubes 122" and reinforcement panels 130 are thereafter cut to their lengths.

Another exemplary magnet apparatus, which is generally represented by reference numeral 100*b* in FIGS. 17-21, is substantially similar to the magnet apparatus 100 and similar elements are represented by similar reference numerals. To that end, the magnet apparatus 100*b* includes a case 102*b*, with a base 104*b* and a cover 106*b*, a frame 108*b*, and a magnet subassembly 110*b*. Here, however, the magnet subassembly 110*b* includes four relatively long magnets 112' and the frame 108*b* has four relatively long tubes 122'. There are also two relatively short magnets 112" and two relatively short tubes 122". Although some implementations of a six-magnet subassembly may have a pre-set arcuate shape similar to that illustrated in FIG. 5, the exemplary magnet subassembly 110*b* has a flat shape. When the holder 114*b* is in a relaxed, i.e., unstressed, state the longitudinal axis A2 of each tube 112 is located in the same horizontal plane HP. The flat shape facilitates the use of a thinner case 102*b*, although the flat shape also results is more friction between the magnet subassembly 110*b* and the case 102*b*, as compared to an arcuate magnet subassembly.

The tubes 122 include cylindrical walls 123 and adjacent tubes 122 of the exemplary magnet holder 114*b* share common wall portions 123*c* at locations along the horizontal plane HP, thereby reducing the overall width of the holder 114. For example, the thickness of wall portions 123_c_ at the horizonal plane HP may be the same as the thickness of the remainder of the cylindrical walls 123. The joints 126_b_ of the exemplary magnet holder 114_b_ are thicker than the joints 126 of the magnet holder 114, i.e., there is more material above and below the horizontal plane HP, without increasing the distance between adjacent lumens 124. The thicker joints 126_b_ allow the magnet holder 114_b_ to better resist bending when subjected to strong magnetic fields.

Another exemplary magnet apparatus is generally represented by reference numeral 100_c_ in FIGS. 22-25. Magnet apparatus 100_c_ is substantially similar to magnet apparatus 100 and similar elements are represented by similar reference numerals. For example, the magnet apparatus 100_c_ includes a case 102, with a base 104 and a cover 106, a frame 108, and a magnet subassembly 110_c_. Here, however, the magnet subassembly 110_c_ includes a more robust injection molded magnet holder 114_c_ that is not susceptible to ovaling associated with individual tubes. The exemplary holder 114_c_ includes a relatively long rectangular portion 121_c_' that defines a plurality of tubes 122_c_' with lumens 124 for the relatively long magnets 112' and a pair of relatively short rectangular portions 121_c_" that define respective tubes 122_c_" with lumens 124 for the relatively short magnet 112". The holder 114_c_ has a flat shape and the longitudinal axis of each tube 112 is located in the same horizontal plane. As noted above, suitable materials for the holder 114_c_ include those discussed above with reference to the holder 114. By way of example, but not limitation, the holder 114_c_ may be injection molded from PEEK. In the exemplary context of PEEK, the molded holder 114_c_ may be easier to manufacture than an extruded PEEK holder (such as holder 114) that requires some of the tubes 122 to be trimmed down to a shorter length after the extrusion.

Figure 26:
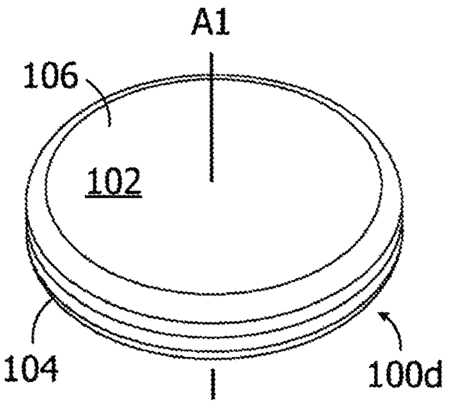
FIG. 26 is a perspective view of an implant magnet apparatus in accordance with one embodiment of a present invention.
Figure 27:
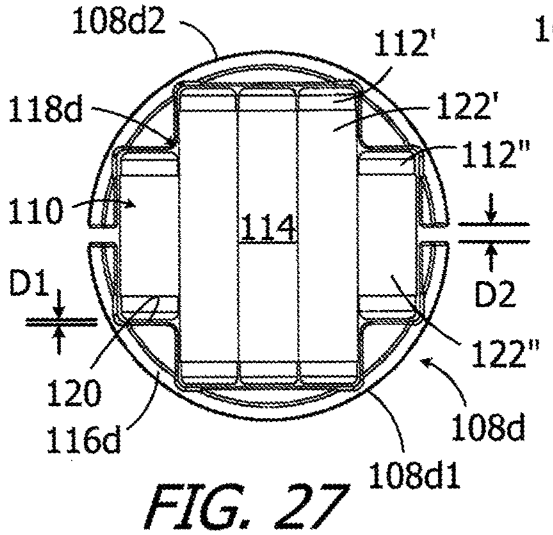
FIG. 27 is a top view of a portion of the implant magnet apparatus illustrated in FIG. 26.
Figure 28:
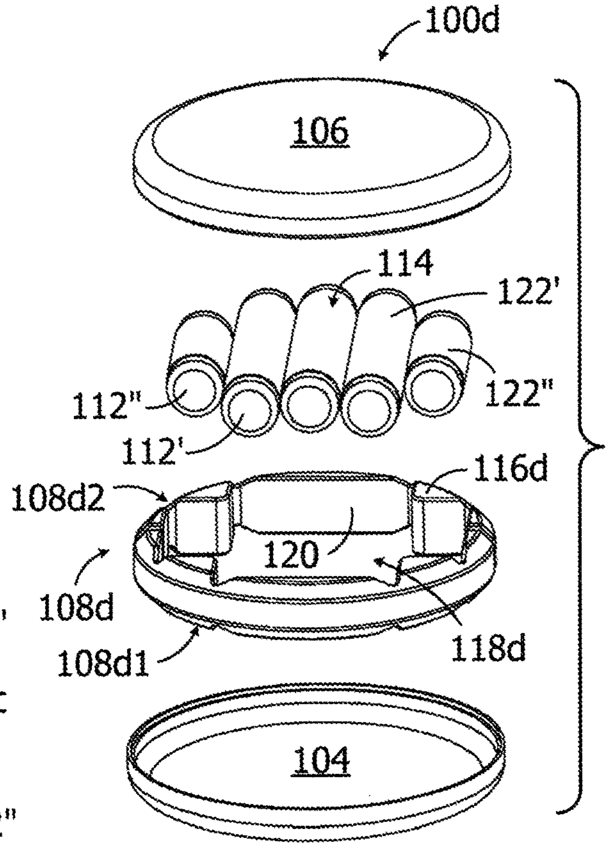
FIG. 28 is an exploded perspective view of the implant magnet apparatus illustrated in FIG. 26.

The exemplary magnet apparatus 100_d_ illustrated in FIGS. 26-28 is substantially similar to the magnet apparatus 100 and similar elements are represented by similar reference numerals. To that end, the magnet apparatus 100_d_ includes a case 102, with a base 104 and a cover 106, a frame 108_d_, and a magnet subassembly 110 with a magnet holder 114 and a plurality of magnets 112. Here, however, the frame 108_d_ includes two separate frame members 108_d_1 and 108_d_2. Each of the frame members 108_d_1 and 108_d_2 includes a partial disk 116_d_ with inner walls 120 and has an overall C-shape with a curve end and two free ends. When the separate partial disks 116_d_ are positioned adjacent to one another in the manner illustrated in FIGS. 27 and 28, the partial disks will together define a magnet receptacle 118_d_ that extends completely through the frame 108_d_ and is defined by the inner walls 120. The case 102, magnets 112 and the frame 108_d_ are respectively sized such that, when the magnet assembly 110 is located within the magnet receptacle 118_d_, the free ends of the frame members 108_d_1 and 108_d_2 will face one another and will be separated from one another by a distance D2, while the longitudinal ends of the magnets 112 will be separated from the inner walls 120 by distance D1. Distance D1 may be about 0.08 to 0.15 in some implementations and distance D2 may be about 0.2 to 0.6 in some implementations as noted above.

Figure 29:
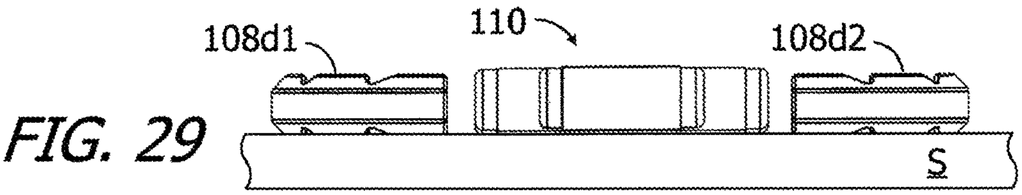
FIGS. 29-30 are side and top views showing an exemplary method of assembling a portion of the implant magnet apparatus illustrated in FIG. 26.
Figure 30:
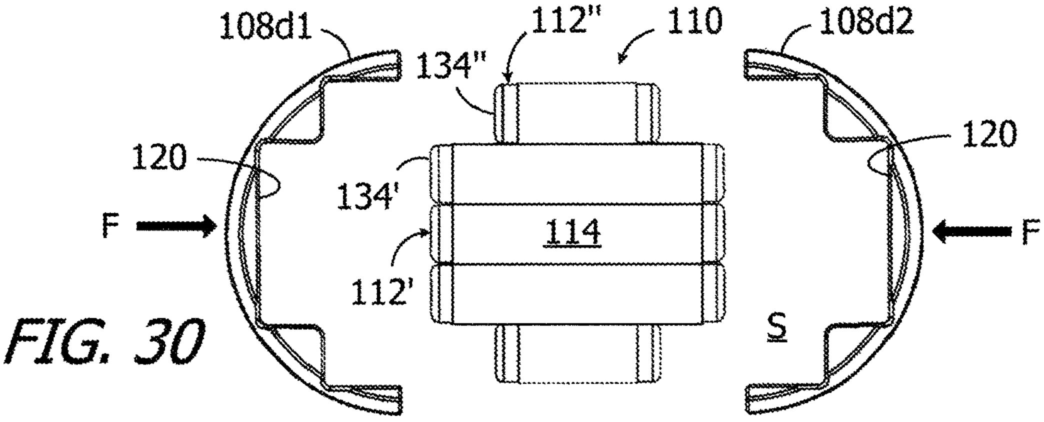

Referring to FIGS. 29 and 30, the exemplary magnet assembly 110 may be combined with the exemplary frame members 108_d_1 and 108_d_2 by placing the magnet assembly and the frame members on a surface S with the frame members on opposite sides of the magnet assembly and the frame member inner walls 120 facing the longitudinal ends 134 and 136 of the magnets 112' and 112". The frame members 108_d_1 and 108_d_2 may then be pushed toward one another, by applying a force F thereto, until the frame members abut the magnet assembly 110 in the manner illustrated in FIGS. 27 and 28. The magnet assembly 110 and frame 108_d_ may then be transferred to the case base 104, and the case cover 106 may thereafter be secured to the case base to complete the magnet apparatus.

Figure 31:
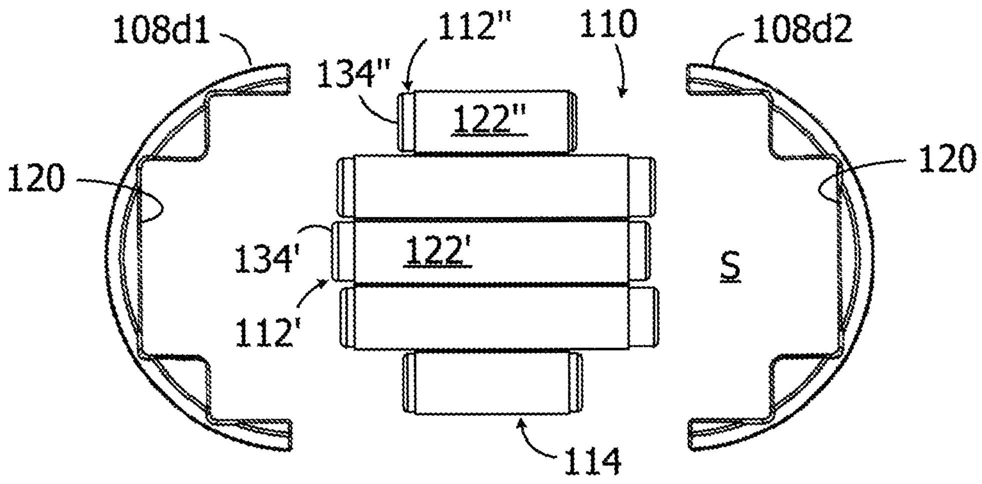
FIGS. 31-33 are top views showing an exemplary method of assembling a portion of the implant magnet apparatus illustrated in FIG. 26.
Figure 32:
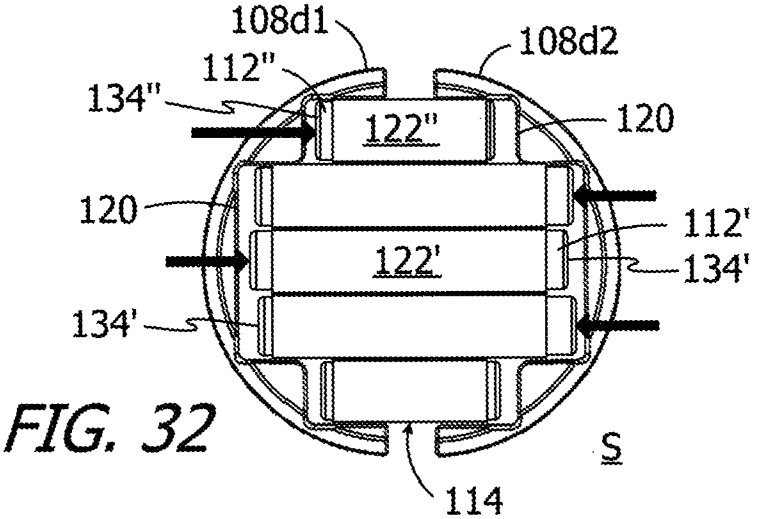
Figure 33:
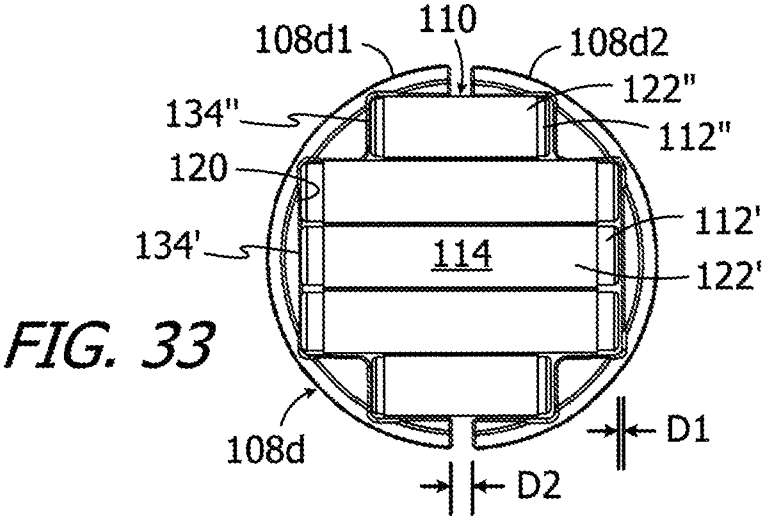

There are a number of advantages associated with the exemplary frame 108_d_ and the manner in which it may be combined with the magnet assembly 110. For example, inserting a magnet assembly 110 into a one-piece frame such as that illustrated in FIGS. 2-4 can be difficult due to the relatively tight fit between magnet assembly and the receptacle 118. Even when the longitudinal ends 134' and 134" of the magnets 112' and 112" are properly aligned with one another and the magnets are centered relative to the tubes 122' and 122" as is shown in FIGS. 29 and 30, it can be difficult to place the magnet assembly 110 into a one-piece frame. The frame members 108_d_1 and 108_d_2 may also be used to properly position the magnets 112 in those instances where the magnets are not properly aligned and centered. To that end, FIG. 31 shows an exemplary instance of a magnet assembly 110 with magnets 112 that are not properly aligned with one another and centered relative to the tubes 122 of the magnet holder 114. In particular, the longitudinal ends 134' of the relatively long magnets 112' are not properly aligned with one another, the longitudinal ends 134" of the relatively short magnets 112" are not properly aligned with one another, and not all of the magnets are centered relative to the associated magnet holder tube 120. As the frame members 108_d_1 and 108_d_2 are moving toward one another in the manner illustrated in FIG. 32, the frame members will eventually come into contact with the ends 134' and 134" of the misaligned magnets at the locations identified by the arrows. Continued movement of the frame members 108_d_1 and 108_d_2 will result in a complete frame 108_d_ and a magnet subassembly 110 with magnets 112 that are properly positioned relative to the magnet holder 114.

Figure 34:
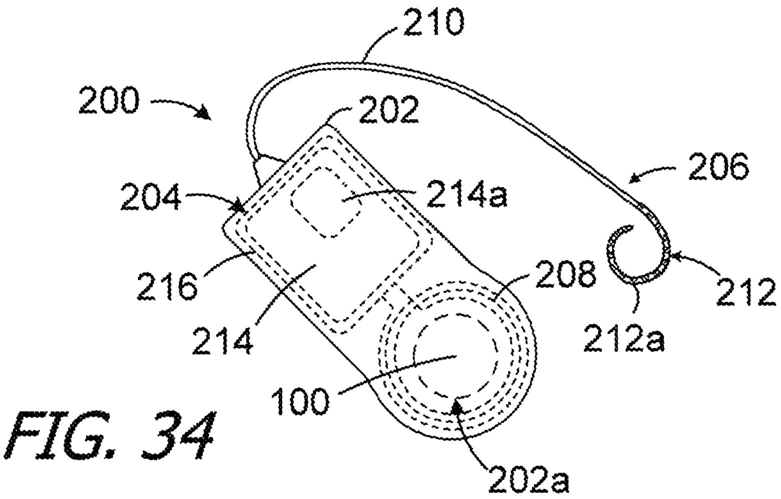
FIG. 34 is a top view of a cochlear implant in accordance with one embodiment of a present invention.

One example of a cochlear implant (or "implantable cochlear stimulator") including the present magnet apparatus 100 (or 100_b_-100_d_) is the cochlear implant 200 illustrated in FIG. 34. The cochlear implant 200 includes a flexible housing 202 formed from a silicone elastomer or other suitable material, a processor assembly 204, a cochlear lead 206, and an antenna 208 that may be used to receive data and power by way of an external antenna that is associated with, for example, a sound processor unit. The cochlear lead 206 may include a flexible body 210, an electrode array 212 at one end of the flexible body, and a plurality of wires (not shown) that extend through the flexible body from the electrodes 212_a_ (e.g., platinum electrodes) in the array 212 to the other end of the flexible body. The magnet apparatus 100 is located within a region encircled by the antenna 208 (e.g., within an internal pocket 202_a_ defined by the housing 202) and insures that an external antenna (discussed below) will be properly positioned relative to the antenna 208. The exemplary processor assembly 204, which is connected to the electrode array 212 and antenna 208, includes a printed circuit board 214 with a stimulation processor 214_a_ that is located within a hermetically sealed case 216. The stimulation processor 214_a_ converts the stimulation data into stimulation signals that stimulate the electrodes 212_a_ of the electrode array 212.

Figure 35:
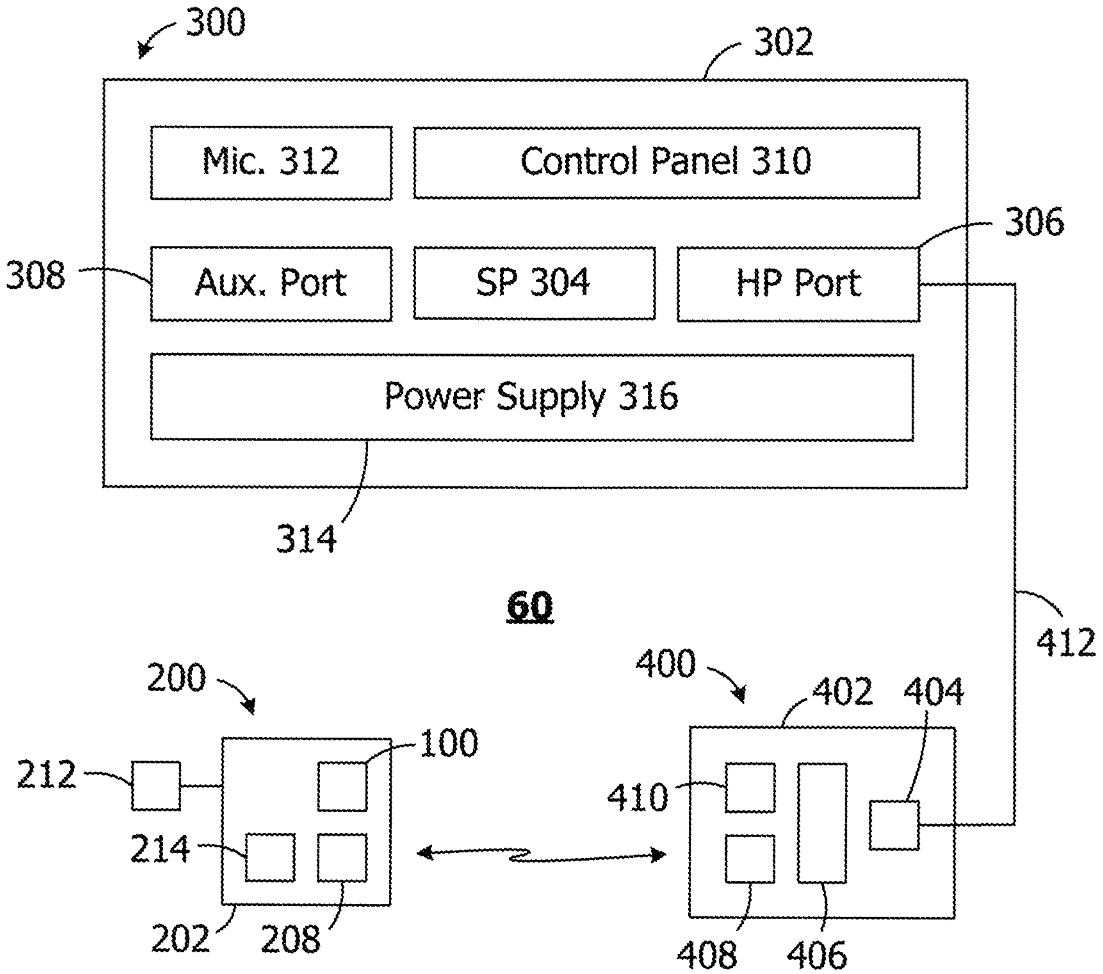
FIG. 35 is a block diagram of a cochlear implant system in accordance with one embodiment of a present invention.

Turning to FIG. 35, the exemplary cochlear implant system 60 includes the cochlear implant 200, a sound processor, such as the illustrated body worn sound processor 300 or a behind-the-ear sound processor, and a headpiece 400.

The exemplary body worn sound processor 300 in the exemplary ICS system 60 includes a housing 302 in which and/or on which various components are supported. Such components may include, but are not limited to, sound processor circuitry 304, a headpiece port 306, an auxiliary device port 308 for an auxiliary device such as a mobile phone or a music player, a control panel 310, one or more microphones 312, and a power supply receptacle 314 for a removable battery or other removable power supply 316 (e.g., rechargeable and disposable batteries or other electrochemical cells). The sound processor circuitry 304 converts electrical signals from the microphone 312 into stimulation data. The exemplary headpiece 400 includes a housing 402 and various components, e.g., a RF connector 404, a microphone 406, an antenna (or other transmitter) 408 and a diametrically magnetized disk-shaped positioning magnet 410, that are carried by the housing. The headpiece 400 may be connected to the sound processor headpiece port 306 by a cable 412. The positioning magnet 410 is attracted to the magnet apparatus 100 of the cochlear stimulator 200, thereby aligning the antenna 408 with the antenna 208. The stimulation data and, in many instances power, is supplied to the headpiece 400. The headpiece 400 transcutaneously transmits the stimulation data, and in many instances power, to the cochlear implant 200 by way of a wireless link between the antennae. The stimulation processor 214*a* converts the stimulation data into stimulation signals that stimulate the electrodes 212*a* of the electrode array 212.

In at least some implementations, the cable 412 will be configured for forward telemetry and power signals at 49 MHz and back telemetry signals at 10.7 MHz. It should be noted that, in other implementations, communication between a sound processor and a headpiece and/or auxiliary device may be accomplished through wireless communication techniques. Additionally, given the presence of the microphone(s) 312 on the sound processor 300, the microphone 406 may be also be omitted in some instances. The functionality of the sound processor 300 and headpiece 400 may also be combined into a single head wearable sound processor. Examples of head wearable sound processors are illustrated and described in U.S. Pat. Nos. 8,811,643 and 8,983,102, which are incorporated herein by reference in their entirety.

Although the inventions disclosed herein have been described in terms of the preferred embodiments above, numerous modifications and/or additions to the above-described preferred embodiments would be readily apparent to one skilled in the art. The inventions include any combination of the elements from the various species and embodiments disclosed in the specification that are not already described. It is intended that the scope of the present inventions extend to all such modifications and/or additions and that the scope of the present inventions is limited solely by the claims set forth below.

We claim:

1. A magnet apparatus, comprising:

a case defining a central axis having a central axis direction;

a frame, defining a receptacle that extends in the central axis direction completely through the frame, within the case and rotatable about the central axis of the case;

a magnet holder within the receptacle and including a plurality of parallel tubes that together define an integral structure; and a plurality of elongate diametrically magnetized magnets within the case that are respectively located in the plurality of tubes, each of the magnets defining a longitudinal axis and a N-S direction and being rotatable about the longitudinal axis relative to the tubes.

2. A magnet apparatus as claimed in claim 1, wherein the frame comprises a single disk.

3. A magnet apparatus as claimed in claim 1, wherein the frame includes two separate and spaced apart frame members that together define the magnet receptacle.

4. A magnet apparatus as claimed in claim 1, wherein the magnet holder is formed from lubricious material.

5. A magnet apparatus as claimed in claim 1, wherein the magnet holder defines a curved shape.

6. A magnet apparatus as claimed in claim 5, wherein the tubes each define a longitudinal axis; and at least one of the longitudinal axes is located on a horizontal plane when the magnet holder is in a relaxed state; and not all of the longitudinal axes are located on the horizontal plane.

7. A magnet apparatus as claimed in claim 5, wherein the tubes each define a longitudinal axis; and the longitudinal axes together define a curve in a plane perpendicular to the longitudinal axes when the magnet holder is in a relaxed state.

8. A magnet apparatus as claimed in claim 1, wherein at least one reinforcement panel is secured to at least two of the tubes.

9. A magnet apparatus as claimed in claim 1, wherein the tubes include cylindrical walls; and at least two adjacent tubes share a common cylindrical wall portion.

10. A magnet apparatus as claimed in claim 1, wherein the magnet holder includes a relatively long rectangular portion that defines a plurality of the tubes and a pair of relatively short rectangular portions that each define a respective one of the tubes.

11. A magnet apparatus as claimed in claim 1, wherein the magnets each define a N-S rotational orientation; and the magnets are magnetically attracted to one another in such manner that, absent the presence of a dominant magnetic field, the N-S rotational orientation of the magnets is at least substantially perpendicular to the central axis of the case.

12. A magnet apparatus as claimed in claim 1, wherein the longitudinal axes of the magnets are at least substantially perpendicular to the central axis.

13. A magnet apparatus as claimed in claim 1, wherein the longitudinal axes of the all of the magnets within the case are parallel to one another.

14. A magnet apparatus comprising:

a case defining a central axis and an inner surface;

a frame, defining a receptacle, within the case and rotatable about the central axis of the case;

a magnet holder within the receptacle and including a plurality of tubes that together define an integral structure; and a plurality of elongate diametrically magnetized magnets that are respectively located in the plurality of tubes, the magnets defining a longitudinal axis and a N-S direction and being rotatable about the longitudinal axis relative to the tubes;

wherein at least some of the tubes are in contact with the inner surface of the case when the magnet holder is in a relaxed state; and at least some of the tubes are not in contact with the inner surface of the case when the magnet holder is in the relaxed state.

15. A magnet apparatus as claimed in claim 14, wherein the frame comprises a single disk; and the receptacle extends completely through the single disk.

16. A magnet apparatus as claimed in claim 14, wherein the frame includes two separate and spaced apart frame members that together define the magnet receptacle.

17. A magnet apparatus as claimed in claim 14, wherein the magnet holder is formed from lubricious material.

18. A magnet apparatus as claimed in claim 14, wherein the magnet holder defines a curved shape.

19. A magnet apparatus as claimed in claim 18, wherein the tubes each define a longitudinal axis; and at least one of the longitudinal axes is located on a horizontal plane when the magnet holder is in a relaxed state; and not all of the longitudinal axes are located on the horizontal plane.

20. A magnet apparatus as claimed in claim 18, wherein the tubes each define a longitudinal axis; and the longitudinal axes together define a curve in a plane perpendicular to the longitudinal axes when the magnet holder is in a relaxed state.

21. A magnet apparatus as claimed in claim 14, wherein the longitudinal axes of the magnets are at least substantially perpendicular to the central axis.

* * * * *